United States Patent
Kobayashi et al.

[11] Patent Number: 5,332,734
[45] Date of Patent: Jul. 26, 1994

[54] OXAZINONE DERIVATIVE

[75] Inventors: Koji Kobayashi; Shunichi Manabe; Yoshihiro Watanabe; Kazuhide Hayakawa; Itsuo Uchida, all of Yokohama, Japan

[73] Assignee: Japan Tobacco, Incorporated, Tokyo, Japan

[21] Appl. No.: 956,029
[22] PCT Filed: Apr. 9, 1992
[86] PCT No.: PCT/JP92/00444
§ 371 Date: Dec. 10, 1992
§ 102(e) Date: Dec. 10, 1992
[87] PCT Pub. No.: WO92/18488
PCT Pub. Date: Oct. 29, 1992

[30] Foreign Application Priority Data

Apr. 10, 1991 [JP] Japan .................. 3-164060

[51] Int. Cl.$^5$ ............... C07D 239/95; C07D 239/72; A61K 31/54; A61K 31/535
[52] U.S. Cl. ...................... 514/225.2; 514/230.5; 544/46; 544/92
[58] Field of Search ............ 544/92, 46; 514/230.5, 514/225.2

[56] References Cited

U.S. PATENT DOCUMENTS

| | | | |
|---|---|---|---|
| 4,013,665 | 3/1977 | Crenshaw et al. | 544/92 |
| 4,980,287 | 12/1990 | Kokubo et al. | 514/2 |
| 5,179,091 | 1/1993 | Lesieur et al. | 514/224.5 |
| 5,204,462 | 4/1993 | Kobayashi et al. | 544/92 |

FOREIGN PATENT DOCUMENTS

| | | |
|---|---|---|
| 0337549 | 10/1989 | European Pat. Off. |
| 1308227 | 12/1989 | Japan . |
| 8809790 | 12/1988 | World Int. Prop. O. |

OTHER PUBLICATIONS

Krantz et al., Journal of Medicinal Chemistry, vol. 33, No. 2, Feb. 1990, pp. 464–479.
Horwitz et al, Journal of Rheunatology, vol. 14 (supp. 13) pp. 49–52, 1987.
Teshima et al, Journal of Biological Chemistry, vol. 257, No. 9, pp. 5085–5091, May 10, 1982.
Cook et al, J. Med. Chem., 30, pp. 1017–1023, 1987.
Miyano et al., J. Med. Chem., 31, pp. 1052–1061, 1988.
Krantz et al, J. Med. Chem., 33, pp. 464–479, 1990.

*Primary Examiner*—Mukund J. Shah
*Assistant Examiner*—Matthew V. Grumbling
*Attorney, Agent, or Firm*—Birch, Stewart, Kolasch & Birch

[57] ABSTRACT

Disclosed is a novel oxazinone derivative represented by formula (I) given below or a pharmaceutically acceptable acid-addition salt thereof, which is useful as an anti-inflammatory agent, an agent for suppressing neutrophil infiltration and as a serine protease inhibitor:

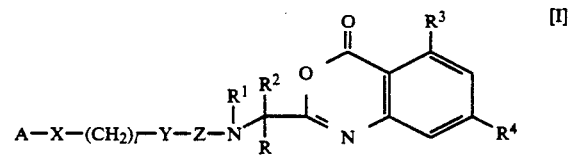

where A includes, for example,

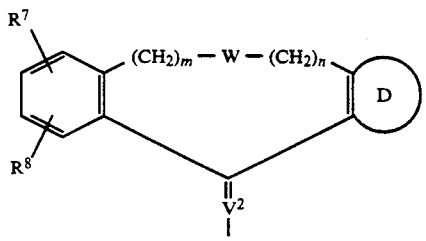

in which W is —O—, —S—, —CH=CH— or —NR$^9$— or means that (CH$_2$)$_n$ is directly bonded to (CH$_2$)$_n$,
V$^2$ is =CR$^{12}$— or =N—, and
D is 5 to 7-membered carbon ring or hetero ring;
X is —O—, —S—, —CO—, or —NR$^{15}$ or means that A is directly bonded to (CH$_2$)$_l$;
Y is —O—, —CH=CH— or —NR$^{16}$— or means that (CH$_2$)$_l$ is directly bonded to Z;
Z is —CH$_2$— or —CO—; and
l is an integer of 0 to 4.
Further, R and R$^1$ to R$^{16}$ are hydrogen atom, lower alkyl group, etc.

4 Claims, No Drawings

OXAZINONE DERIVATIVE

TECHNICAL FIELD

The present invention relates to a novel oxazinone derivative, which has an anti-inflammatory action, a neutrophil infiltration-suppressing action or a serine protease inhibiting action and, thus, is useful in the medical field.

BACKGROUND ART

Infiltration of immunocompetent cells, particularly neutrophils, from blood into tissues, which characterizes the basic morbidity of inflammation, is deeply implicated to the formation of edema caused by the subsequent leakage of blood components and to the progress of the inflammatory symptoms accompanying with the tissue destruction. The diseases in which the abnormality of immunity is considered to be involved in the progress of the inflammatory symptoms include, for example, non-specific inflammatory diseases such as chronic arthritis; diseases of respiratory organs such as chronic obstructive pulmonary disease and pulmonary bronchitis based on chronic respiratory tract infection, adult respiratory distress syndrome, and bronchi-obstructive type asthma classified as the adult type asthma; colon disease which is one of intestinal diseases; and psoriasis which is one of dermatitis.

In addition to various inflammatory cytokine and chemical mediators produced by neutrophils, proteases are considered to play a significant role in the induction of edema and inflammatory symptoms accompanying with tissue destruction, which follow the neutrophile infiltration. Protease is an enzyme serving to degrade elastin and collagen as fiber proteins constituting interstitial connective tissue in organs such as lung, cartilage, blood vessel wall and skin of higher animals. Moreover, protease possesses cytotoxic activity to cells of higher animals. In particular, elastase, i.e., a protease which degrades elastin, is considered to play a great important role. Such being the situation, an elastase inhibitor has come to be hopefull to become an effective prophylatic and therapeutic agent for the above-noted diseases, as well as for various diseases including pancreatitis, nephritis, arteriosclerosis and septicemia, due to the destruction and deterioration of tissue caused by elastase and the cytotoxity of the elastase.

Some peptide or non-peptide compounds have already been reported as serine protease inhibitors such as elastase inhibitor. For example, non-peptide inhibitors are reported in "Journal of the Biochemistry, Vol. 257, pages 5085 to 5091 (1982)", "Journal of the Medicinal Chemistry, Vol. 30, pages 1017 to 1023 (1987)", "Journal of the Medicinal Chemistry, Vol. 31, pages 1052 to 1061 (1988)", "Journal of the Medicinal Chemistry, vol. 33, pages 464 to 479 (1990)", Published Unexamined Japanese Patent Application No. 1-308227, WO 88/9790, and EPO 337549.

On the other hand, a large amount of endogenous protease inhibitors are present together with protease in the inflammatory regions. This may suggest that it is insufficient to utilize the protease inhibitory activity alone for preventing or suppressing the initiation and progression of the inflammation. For example, the hypothesis on the induction of chronic arthritis has been proposed by Lower et al in "Journal of Rheumatol, Vol. 14, page 49 (1987)". It's indicated that activated neutrophils once infiltrating into cartilage, organs and so on, are considered not to be interfered their functions by a protease inhibitor and are considered to cause the destruction of cartilage, organ and so on.

With above informations and a hypothesis together, it is of high demand to develop a medicine which acts as an effective anti-inflammatory agent suppressing the neutrophil function, thereby preventing the infiltration of neutrophils migrating into the inflammatory region and also inhibiting the tissue destruction by the action of elastase excreted from the infiltrated neutrophils.

DISCLOSURE OF THE INVENTION

The present invention, which has been achieved in view of the situation described above, is intended to provide a medicine which acts on each stage of inflammation so as to suppress the tissue destruction.

As a result of an extensive research made in an effort to achieve the object noted above, the present inventors have found a novel oxazinone derivative which has an excellent inhibitory activity relative to serine protease, particularly elastase, serves to suppress chemotaxis of neutrophils in the human peripheral blood against chemical attraction substances derived from bacteria, and has an activity for suppressing the neutrophil infiltration in an animal inflammation model, arriving at the present invention.

According to an aspect of the present invention, there is provided a novel oxazinone derivative represented by formula [I] given below or a pharmaceutically acceptable acid-addition salt thereof:

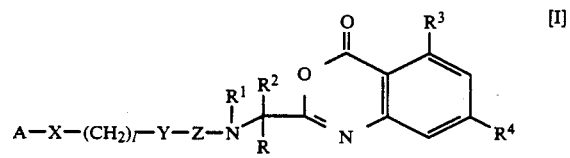

where $R^1$ is hydrogen atom, lower alkyl group or lower acyl group;

R and $R^2$ which are the same or different, are hydrogen atom, lower alkyl group or lower alkylthio lower alkyl group, and possibly form together an alicyclic ring;

$R^3$ is hydrogen atom, lower alkyl group which may be substituted with fluorine, or lower alkoxy group or halogen atom;

$R^4$ is hydrogen atom, lower alkyl group, hydroxyl group, halogen atom, lower alkoxy group, lower alkoxycarbonyl group, carboxyl group, lower alkylthio group, nitro group, lower acyloxy group or $-NR^5R^6$ ($R^5$ and $R^6$, which are the same or different, being hydrogen atom, lower alkyl group or lower acyl group, or $R^5$ and $R^6$ forming a hetero ring together with the adjacent nitrogen atom, said hetero ring may being substituted);

A is

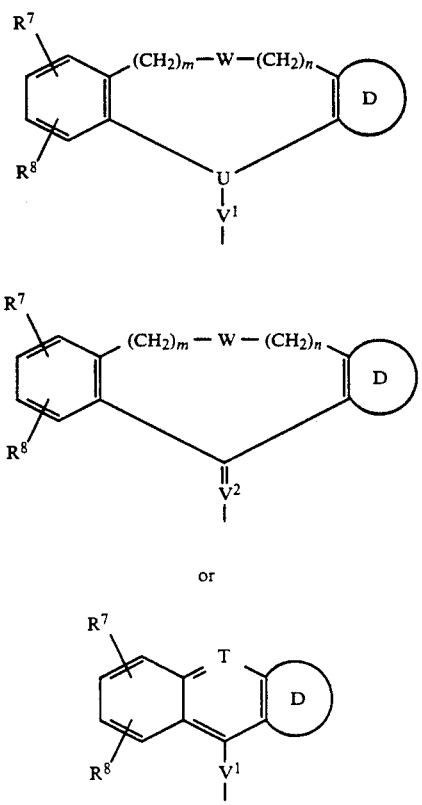

in which
W is —O—, —S—, —CH=CH—, or —NR$^9$ (R$^9$ being hydrogen atom, lower alkyl group or lower acyl group) or means that (CH)$_m$ is directly bonded to (CH$_2$)$_n$;
U is

or nitrogen atom;
V$^1$ is —O—, —S—, —CO—, —CHR$^{10}$— (R$^{10}$ being hydrogen atom, lower alkyl group or lower acyl group), or —NR$^{11}$— (R$^{11}$ being hydrogen atom, lower alkyl group or lower acyl group), with proviso that when U is nitrogen atom, V$^1$ is —CO—, or —CHR$^{10}$— (R$^{10}$ being as defined above) or —NR$^{11}$— (R$^{11}$ being as defined above);
V$^2$ is =CR$^{12}$— (R$^{12}$ being hydrogen atom, lower alkyl group or lower acyl group) or =N—;
T is =CH— or =N—;
R$^7$ and R$^8$, which are the same or different, are hydrogen atom, lower alkyl group which may be substituted with fluorine, lower acyl group, halogen atom, hydroxyl group, lower alkoxy group, lower acyloxy group, carboxyl group or —NR$^{13}$R$^{14}$ (R$^{13}$ and R$^{14}$, which are the same or different, being hydrogen atom, lower alkyl group or lower acyl group);
m and n are independently integers of 0 to 2, and m+n≦2; and
D is a 5 to 7-membered aromatic or alicyclic ring which may have at most two substituent groups and may have a plurality of hetero atoms;

X is —O—, —S—, —CO— or —NR$^{15}$— (R$^{15}$ being hydrogen atom, lower alkyl group or lower acyl group) or means that A is directly bonded to (CH$_2$)$_i$;
Y is —O—, —CH=CH— or —NR$^{16}$— (R$^{16}$ being hydrogen atom, lower alkyl group or lower acyl group) or means that (CH$_2$)$_l$ is directly bonded to Z;
Z is —CH$_2$— or —CO—, with the proviso that when Z is —CH$_2$—, (CH$_2$)$_l$ is directly bonded to Z; and
l is an integer of 0 to 4.

According to another aspect of the present invention, there are provided an anti-inflammatory agent, an agent for suppressing neutrophil infiltration, and a serine protease inhibitor.

Let us describe in detail the present invention.
The terms used in the present specification are defined as follows:

"Lower Alkyl Group" is a linear or branched alkyl group having 1 to 5 carbon atoms. Specific examples of the lower alkyl group include, for example, methyl, ethyl, propyl, isopropyl, butyl, isobutyl, sec-butyl, tert-butyl, pentyl, and isopentyl group.

"Lower Alkylthio Lower Alkyl Group" is an alkylthio alkyl group having, as a constitutional unit, a linear or branched lower alkyl group having 1 to 5 carbon atoms. Specific examples include (methylthio)methyl, 2-(methylthio)ethyl, (ethylthio)methyl, 2-(ethylthio)ethyl, 1-(ethylthio)ethyl and (isopropylthio)methyl group.

"Alicyclic ring formed by R together with R$^2$" includes, for example, a cyclopropane ring, a cyclobutane ring, a cyclopentane ring and a cyclohexane ring.

"Halogen Atom" includes fluorine, chlorine, bromine and iodine.

"Lower Alkoxy Group" represents a hydroxyl group whose hydrogen atom has been substituted with a linear or branched alkyl chain having 1 to 5 carbon atoms. Specific examples include methoxy, ethoxy, propoxy, isopropoxy, butoxy, isobutoxy, sec-butoxy and pentyloxy group.

"Lower Alkoxy Carbonyl Group" includes, for example, methoxycarbonyl, ethoxycarbonyl, propoxycarbonyl, isopropoxycarbonyl, butoxycarbonyl, sec-butoxycarbonyl and tert-butoxycarbonyl group.

"Lower Acyl Group" represents a linear or branched acyl group having 1 to 5 carbon atoms. Specific examples include formyl, acetyl, propionyl, butyryl, isobutyryl, valeryl and isovaleryl group.

"Lower Acyloxy Group" represents a hydroxyl group whose hydrogen atom has been substituted with "Lower Acyl Group" defined above. Specific examples are acetoxy, ethylcarbonyloxy, propylcarbonyloxy, isopropylcarbonyloxy, butylcarbonyloxy, isobutylcarbonyloxy, sec-butylcarbonyloxy, and isopentylcarbonyloxy group.

"Lower Alkylthio Group" represents a thiol group whose hydrogen atom has been substituted with a linear or branched alkyl chain having 1 to 5 carbon atoms. Specific examples include methylthio, ethylthio, propylthio, isopropylthio, butylthio, tert-butylthio, pentylthio, and isopentylthio group.

As described previously, D is defined to be a 5 to 7-membered aromatic or alicyclic ring which may have at most two substituent groups and may have a plurality of hetero atoms. Specific examples of D include:

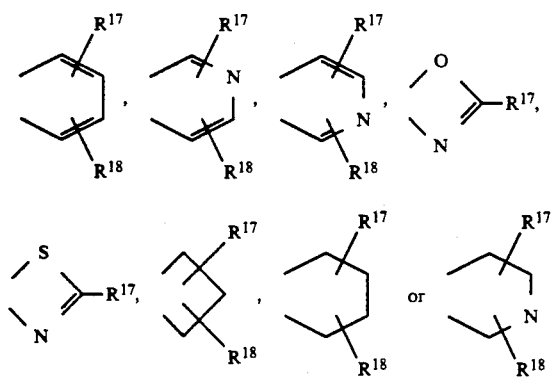

where each of $R^{17}$ and $R^{18}$, which are the same or different, is hydrogen atom, a lower alkyl group which may be substituted with fluorine, lower acyl group, halogen atom, hydroxyl group, lower alkoxy group, lower acyloxy group, carboxyl group or —$NR^{19}R^{20}$ (each of $R^{19}$ and $R^{20}$, which may be the same or different, being hydrogen atom, lower alkyl group or lower acyl group).

The novel oxazinone derivative of the present invention represented by formula [I] can be prepared by the methods exemplified below, though a method for preparing the particular oxazinone derivative of the present invention is not restricted thereto. The definitions of A, X, Y, Z, R, $R^1$, $R^2$, $R^3$, $R^4$ and l included in the reaction formulas given below are the same as those given previously. In addition, $L^1$ and $L^2$ are defined as follows:

$L^1$ is hydrogen atom or a carboxyl-protective group generally used for the synthesis of peptide such as ethyl or benzyl group; and $L^2$ is an amino-protective group generally used for the synthesis of peptide such as benzyloxycarbonyl or tert-butoxycarbonyl group.

In case of Z is —CO—

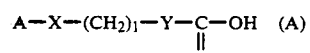
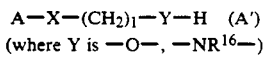
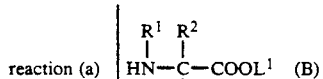
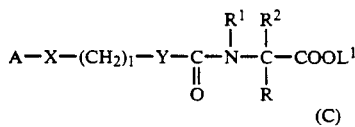
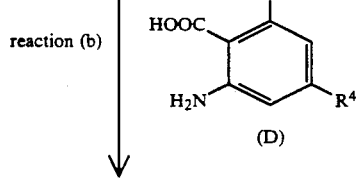
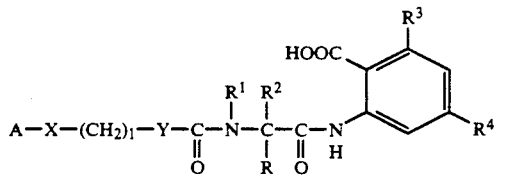
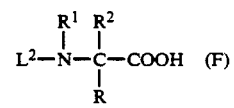
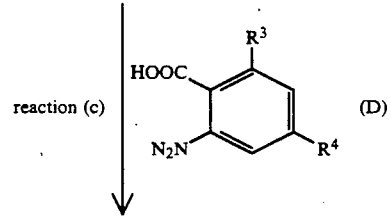
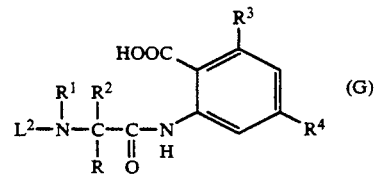
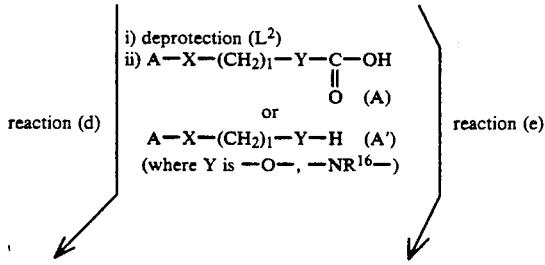
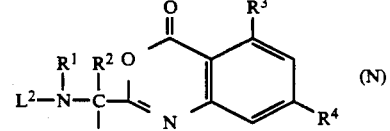

-continued

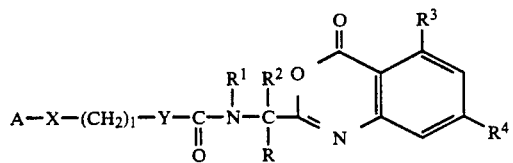

In case of Z is —CH$_2$— ((CH$_2$)$_l$ is directly bonded to Z)

Each step included in the reaction formulas given above is carried out as follows:

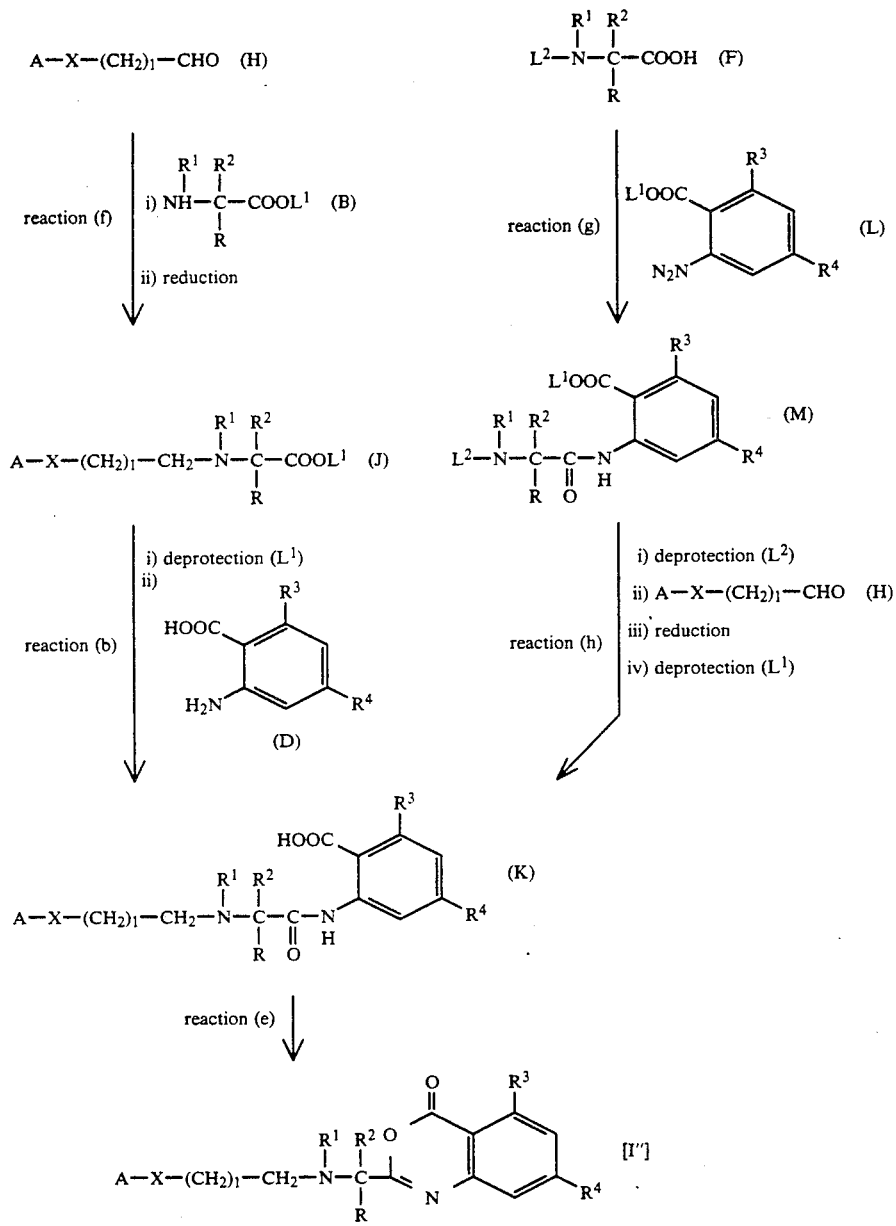

Reactions known as peptide bond-forming reactions in the peptide synthesis, which are described in, for example, "Basic Knowledge and Experiments for Peptide Synthesis" by N. Izumiya et al, published by Maruzen K. K., can be employed in reactions (a) to (e) and (g) included in the reaction formulas given above. Also, known reductive alkylating reaction can be employed in reactions (f) and (h).

(1) Where Z is —CO—:

In reaction (a), a compound A or A' is subjected to a condensation reaction with an amino acid derivative B of which carboxyl group in protected or not as desired so as to give a compound C. The condensation reaction should desirably be carried out as follows.

Specifically, the compound A is reacted with monoalkyl carbonate such as isobutyl chloroformate in an inert organic solvent in the presence of a tertiary amine such as triethylamine, N-methylmorpholine so as to give an mixed acid anhydride. Then, the mixed anhydride, which is not isolated, is subjected to a condensation reaction with the amino acid derivative B. Alternatively, a reaction between the compound A and N-hydroxysuccinimide is carried out within the inert organic solvent in the presence of a dehydration-condensation agent such as water-soluble carbodiimide hydrochloride, e.g., 1-ethyl-3-(3-dimethylaminopropyl) carbodiimide hydrochloride, or N,N'-dicyclohexylcarbodiimide so as to give N-hydroxysuccinimide ester. Then, the ester thus formed is reacted with a compound B in a mixed solvent such as a mixture of water and acetone in the presence of a base such as sodium carbonate so as to give a compound C.

In the case of using the compound A', the compound A' is reacted with phosgene, trichloromethyl chloroformate or carbonyldiimidazole within a suitable solvent such as 1,4-dioxane or tetrahydrofuran in the presence of a tertiary amine such as triethylamine. The reaction is carried out at a temperature falling within a range between −20° C. and room temperature. Then, the reaction mixture is reacted with the compound B so as to give the compound C. Where L$^1$ of the compound B represents a carboxyl-protective group, the compound C can be synthesized by a condensation reaction using, for example, N,N'-dicyclohexylcarbodiimide, in an inert organic solvent in the presence or absence of a suitable additive such as 1-hydroxybenzotriazole.

Where L$^1$ represents a carboxyl protective group, the carboxyl-protective group of the compound C is removed by the ordinary method in reaction (b) so as to convert the protected group into a free carboxyl group. Then, a condensation reaction is carried out between the compound having the free carboxyl group and an amino compound D as in reaction (a) so as to give a compound E.

The compound E can also be synthesized via reactions (c) and (d). In this case, a condensation reaction is carried out as in reaction (a) between the compound D having a free amino group and an amino acid derivative F having a free carboxyl group so as to give a compound G, as denoted by reaction (c). Then, a condensation reaction is carried out between a compound having a free amino group, which is prepared by removing the amino-protective group L$^2$ of a compound G by the ordinary method, and a compound prepared by activating the carboxyl group of the compound A as in reaction (a), so as to give the compound E, as denoted by reaction (d). In the case of using the compound A' in reaction (d), the desired compound E can be obtained by using phosgene, trichloromethyl chloroformate or carbonyldiimidazole, as described previously in conjunction with reaction (a).

In reaction (e), the compound E thus obtained is cyclized by a dehydration-condensation reaction in an inert organic solvent so as to give a desired compound of the present invention represented by formula [I']. In this step, water-soluble carbodiimide hydrochloride, N,N'-dicyclohexylcarbodiimide or the like is used as a condensation agent.

In the above description, the cyclizing reaction to form a benzoxazinone ring is performed in the final step, i.e., reaction (e). Alternatively, the compound G may be subjected in advance to a cyclizing reaction under the conditions similar to those in reaction (e) so as to form a benzoxazinone N. In this case, the benzoxazinone N is reacted with the compound A or A' by the method described previously in conjunction with reaction (d) so as to give the desired compound [I'].

(2) Where Z is —CH$_2$—:

In reaction (f), a reductive alkylation reaction is carried out between an aldehyde H and the amino acid derivative B so as to give a compound J. The reductive alkylation reaction can be performed, for example, as follows. Specifically, the compounds H and B are dissolved in the first step in a solvent such as water, methanol or 1,4-dioxane. These solvents can be used singly or in combination. The reaction between these compounds H and B is carried out under a weakly acidic condition, preferably at pH 5 to 7, at a temperature ranging between −30° C. and room temperature, preferably between 0° C. and room temperature so as to form an imine. Then, the imine thus formed is hydrogenated with catalyst such as platinum or is reduced in the presence of a reducing agent such as sodium borohydride or sodium cyanoborohydride so as to give the compound J.

In the next step, where L$^1$ is a carboxyl protecting group, the carboxyl protecting group L$^1$ of the compound J is removed by a known method, exactly as in reaction (b), followed by a condensation reaction with the amino compound D so as to give a compound K.

The compound K may also be obtained via reactions (g) and (h). In this case, a condensation reaction is carried out as in reaction (a) between the amino acid derivative F having a free carboxyl group and an amino compound L so as to give a compound M, as denoted by reaction (g). Then, a reductive alkylating reaction is carried out exactly as in reaction (f) between a compound having a free amino group, which is obtained by removing the amino protective group L$^2$ from the compound M by a known method, and an aldehyde H, as denoted by reaction (h). Where L$^1$ of the compound thus obtained is a carboxyl protective group, the carboxyl protective group L$^1$ is removed by a known method so as to give the compound K. Where L$^1$ of the compound L is a carboxyl protective group, the compound M can be synthesized by a condensation reaction in an inert organic solvent in the presence or absence of a suitable additive such as 1-hydroxybenzotriazole or N-hydroxy-5-norbornene-2,3-dicarboximide. A condensing agent such as N,N'-dicyclohexylcarbodiimide is used in this condensation reaction.

The compound K thus obtained is subjected to a dehydration condensation reaction exactly as in reaction (e) so as to afford a desired compound of the present invention represented by formula [I"].

The inert organic solvent used in the reactions referred to above can be suitably selected from the group consisting of N,N-dimethylformamide, tetrahydrofuran, 1,4-dioxane, 1,2-dimethoxyethane, methylene chloride and ethyl acetate.

After the reaction, the desired compound is isolated from the reaction mixture and, then, purified. Techniques known in the art including, for example, solvent extraction, column chromatography, and recrystallization can be suitably employed for the isolation and purification.

The compounds A, A', B, D, F, H and L used as the starting materials are commercially available, or can be easily derived or synthesized from known precursor by known methods.

In synthesizing the desired compound represented by formula [I], a protective group may be introduced at a suitable stage and may be removed at a suitable stage, if necessary.

Pharmacologically acceptable salts can be formed from the oxazinone derivative of the present invention represented by formula [I]. These salts include an acid addition salt with an inorganic acid such as hydrochloric acid, sulfuric acid, phosphoric acid or hydrobromic acid, and those with an organic acid such as tartaric acid, maleic acid, fumaric acid, succinic acid, or sulfonic acid. Any of these salts is useful as an anti-inflammatory agent, an agent for suppressing neutrophil infiltration, or a serine protease inhibitor.

Various isomers including, for example, geometric isomers such as cis- and trans-isomers may be present in the oxazinone derivative of the present invention represented by formula [I]. Where asymmetric carbon atoms are contained in the oxazinone derivative, stereoisomers based on these asymmetric carbon atoms such as enantiomer and diasteromer are included in the oxazinone derivative of the present invention. Of course, these isomers and mixtures thereof are included in the scope of the present invention.

The oxazinone derivative represented by formula [I] and salts thereof can be used as an effective ingredient of medicines. The medicine containing the oxazinone derivative or salt thereof is effective as a prophylactic or therapeutic agent for various non-specific inflammatory diseases such as chronic arthritis, which is an inflammatory disease caused by abnormality of immunity; diseases of respiratory organs such as chronic obstructive pulmonary disease and pulmonary bronchitis based on chronic respiratory tract infection, adult respiratory distress syndrome, bronchi-obstructive type asthma classified as the adult type asthma; colon disease which is one of intestinal diseases; and psoriasis which is one of dermatitis. The particular medicine is also effective as a prophylactic or therapeutic agent for the destruction and deterioration of tissue caused by elastase and various diseases including pancreatitis, nephritis, arteriosclerosis and septicemia.

The medicine containing the oxazinone derivative of the present invention represented by formula [I] or a salt thereof can be administered orally or non-orally. It is also possible to administer the medicine via respiratory tract depending on the symptom of the disease.

In the case of the oral administration, the medicine may be used in the form of pillet, capsule, granule, powder or solution. In the case of the non-oral administration, the medicine may be used in the form of a injection formulation, suppository ointment, liquid formulation etc. In preparing the medicine of various forms, an excipient, a binder, a collapsing agent and other additives can be used appropriately by the method known in the art. Particularly, where the medicine is administered via a respiratory tract, it is possible to use a surfactant, a propellant, etc. to form aerosol of the medicine.

The medicine may be administered in an amount of generally 1 to 100 mg/day in terms of the oxazinone derivative represented by formula [I], when the medicine is administered to an adult, though the amount of administration is determined appropriately in view of the age, sex, weight and degree of disease of the patient as well as method of administration.

BEST MODE OF EMBODYING THE INVENTION

Let us describe more in detail the present invention with reference to Examples and Test Examples which follow. Of course, the scope of the present invention is not restricted by these Examples and Test Examples so far as not departing from gist of the present invention.

EXAMPLE 1

Synthesis of 2-{1(S)-[(9-fluorenylmethoxycarbonyl)amino]-2-methylpropyl}-5-methyl-4H-3,1-benzoxazin-4-one (compound 1)

a) Preparation of 2-[(N-benzyloxycarbonyl-L-valyl)amino]-6-methylbenzoic acid 18 ml of acetone and 8.02 g of N-benzyloxycarbonyl-L-valine N-hydroxysuccinimide ester were added to 18 ml of an aqueous solution containing 3.15 g of 2-amino-6-methylbenzoic acid and 2.45 g of sodium carbonate, followed by being kept stirred at room temperature for 5 hours. The mixture was acidified with 1N hydrochloric acid, followed by extraction with ethyl acetate. The organic layer was washed with 1N hydrochloric acid, and saturated saline, dried over anhydrous sodium sulfate, and concentrated. The residue was purified by a silica gel column chromatography to give 3.71 g of 2-[(N-benzyloxycarbnoyl-L-valyl)amino]-6-methylbenzoic acid.

b) Preparation of 6-methyl-2-(L-valylamino)benzoic acid 1.21 g of 2-[(N-benzyloxycarbonyl-L-valyl)amino]-6-methylbenzoic acid was dissolved in a mixture of 99 ml of methanol and 1 ml of water, followed by adding 200 mg of 10% Pd-C. The mixture was stirred for 3 hours at room temperature under a hydrogen atmosphere. Pd-C was filtered off and the filtrate was concentrated to give 830 mg of 6-methyl-2-(L-valylamino)benzoic acid.

c) Preparation of 2-{[N-(9-fluorenylmethoxycarbonyl)-L-valyl]amino}-6-methylbenzoic acid 284 mg of sodium carbonate and 336 mg of 6-methyl-2-(L-valylamino)benzoic acid were dissolved in a mixture consisting of 17 ml of 1,4-dioxane and 12 ml of water, followed by adding dropwise a solution of 345 mg of 9-fluorenylmethoxycarbonyl chloride in 7 ml of 1,4-dioxane under ice-cooling. After stirring for 3.5 hours at room temperature, the reaction mixture was poured into water, acidified with concentrated hydrochloric acid, and extracted with ethyl acetate. The organic layer was washed with a saturated saline, dried over anhydrous magnesium sulfate, and concentrated. The residue was purified by a silica gel column chromatography (eluting solution: hexane-ethyl acetate-acetic acid) to give 460 mg of 2-{[N-(9-fluorenylmethoxy-carbonyl)-L-valyl]amino}-6-methylbenzoic acid.

d) Preparation of 2-{1(S)-[(9-fluorenylmethoxycarbonyl)amino]-2-methylpropyl}-5-methyl-4H-3,1-benzoxazin-4-one 263 mg of N,N'-dicyclohexylcarbodiimide was added under ice-cooling to a solution of 401 mg of 2-{[N-(9-fluorenylmethoxycarbonyl)-L-valyl]amino}-6-methylbenzoic acid in 5 ml of N,N-dimethylformamide. After stirring for 3 hours, dicyclohexyl urea precipitated was filtered off and the filtrate was condensed. The residue was purified by a silica gel column chromatography (eluting solution: hexane-ethyl acetate) to afford 337 mg of 2-{1(S)-[(9-fluorenylmethoxycarbonyl)amino]-2-methylpropyl}-5-methyl-4H-3,1-benzoxazin-4-one, as a white foam. The physicochemical data are shown in Table 1.

EXAMPLE 2

Synthesis of 2-{1(S)-[(9-fluorenylmethoxycarbonyl)amino]-3-methylbutyl}-5-methyl-4H-3,1-benzoxazin-4-one (compound 2)

a) Preparation of 2-{[N-(9-fluorenylmethoxycarbonyl)-L-leucyl]amino}-6-methylbenzoic acid 14 mg of sodium hydride (60% dispersion in mineral oil) was washed three times with n-hexane under an argon atmosphere, followed by adding 5 ml of tetrahydrofuran and 53 mg of 2-amino-6-methylbenzoic acid at room temperature. The mixture was stirred until hydrogen gas generation was ceased, and 200 mg of N-(9-fluorenylmethoxycarbonyl)-L-leucine pentafluorophenyl ester was added. After stirring for 3 hours at room temperature, the reaction mixture was poured into 1N hydrochloric acid and extracted with ethyl acetate. The organic layer was washed with saturated saline, dried over anhydrous magnesium sulfate, and concentrated. The residue was purified by a silica gel column chromatography (eluting solution: hexane-ethyl acetate-acetic acid) to give 184 mg of 2-{[N-(9-fluorenylmethoxycarbonyl)-L-leucyl]amino}-6-methylbenzoic acid.

b) Preparation of 2-{1(S)-[(9-fluorenylmethoxycarbonyl)amino]-3-methylbutyl}-5-methyl-4H-3,1-benzoxazin-4-one 69 mg of N,N'-dicyclohexylcarbodiimide was added under ice-cooling to a solution of 163 mg of 2-{[N-(9-fluorenylmethoxycarbonyl)-L-leucyl]amino}-6-methylbenzoic acid in 4 ml of ethyl acetate. After stirring overnight, dicyclohexylurea precipitated was filtered off and the filtrate was concentrated. The residue was purified by a silica gel column chromatography (eluting solution: hexane-ethyl acetate) to give 110 mg of 2-{1(S)-[(9-fluorenylmethoxycarbonyl)amino]-3-methylbutyl}-5-methyl-4H-3,1-benzoxazine-4-one. The physicochemical data are shown in Table 1.

EXAMPLE 3

Synthesis of 2-{1(S)-[(9-fluorenyloxyacetyl)amino]-2-methylpropyl}-5-methyl-4H-3,1-benzoxazin-4-one (compound 3)

a) Preparation of ethyl 9-fluorenyloxyacetate 0.8 g of sodium hydride (60% dispersion in mineral oil) was added over 5 minutes under ice-cooling to a solution of 3.64 g of 9-fluorenol and 3 ml of ethyl bromoacetate in 40 ml of N,N-dimethylformamide. After stirring for 50 minutes, the reaction mixture was poured into ice-cold 5% HCl and extracted with ether. The organic layer was washed with a saturated saline, dried over anhydrous magnesium sulfate, and concentrated. The residue was purified by a silica gel column chromatography (eluting solution: methylene chloride-hexane) to give 2.28 g of ethyl 9-fluorenyloxyacetate.

b) Preparation of 9-fluorenyloxyacetic acid 10 ml of 1N sodium hydroxide was added dropwise to a solution of 2.28 g of ethyl 9-fluorenyloxyacetate in 40 ml of ethanol, and the mixture was stirred at room temperature for 4 hours. The reaction mixture was concentrated and water was added. After washing with ether, the pH value of the aqueous layer was adjusted with 18% hydrochloric acid to 3 to 4 under ice-cooling, followed by extraction with ether. The organic layer was dried over anhydrous magnesium sulfate, and concentrated to give 1.77 g of 9-fluorenyloxyacetic acid.

c) Preparation of 2-{[N-(9-fluorenyloxyacetyl)-L-valyl]amino}-6-methylbenzoic acid 165 μl of N-methylmorpholine and 181 μl of isobutyl chloroformate were successively added at −15° C. to a solution of 336 mg of 9-fluorenyloxy acetic acid in 5 ml of tetrahydrofuran. After stirring for 0.5 hour, a solution of 250 mg of 6-methyl-2-(L-valylamino)benzoic acid and 135 μl of N-methylmorpholine in 10 ml of N,N-dimethylformamide was added dropwise and the resultant mixture was stirred for 0.5 hour. After stirring for additional 17 hours at room temperature, the reaction mixture was poured into 1N hydrochloric acid and extracted with ethyl acetate. The organic layer was washed with 1N hydrochloric acid, and saturated saline, dried over anhydrous magnesium sulfate, and concentrated. The residue was purified by a silica gel column chromatography (eluting solution: hexane-ethyl acetate-acetic acid) to give 356 mg of a mixture consisting of about 2 parts of 2-{[N-(9-fluorenyloxyacetyl)-L-valyl]amino}-6-methylbenzoic acid and about 1 part of 9-fluorenyloxyacetic acid.

d) Preparation of 2-{1(S)-[(9-fluorenyloxyacetyl)amino]-2-methylpropyl}-5-methyl-4H-3,1-benzoxazin-4-one 139 mg of water-soluble carbodiimide hydrochloride was added under ice-cooling to a solution of 311 mg of the mixture obtained in reaction c) described above in 10 ml of N,N-dimethylformamide. The resultant mixture was stirred at 0° C. for 0.5 hour and, then, at room temperature for 27 hours. The residue obtained by condensing the reaction mixture was purified by a silica gel column chromatography (eluting solution: methylene chloride-ether) to give 204 mg of 2-{1(S)-[(9-fluorenyloxyacetyl)amino]-2-methylpropyl}-5-methyl-4H-3,1-benzoxazin-4-one as a white powder. The physiwchemical data are shown in Table 1.

EXAMPLE 4

Synthesis of 2-[1(S)-[[N-(9-fluorenylcarbonyl)glycyl]amino]-2-methylpropyl]-5-methyl-4H-3,1-benzoxazin-4-one (compound 4)

a) Preparation of methyl N-(9-fluorenylcarbonyl)glycinate 1.2 ml of triethylamine and 1.31 g of 1-hydroxybenzotriazole were successively added, under ice-cooling, to a solution of 1.5 g of fluorene-9-carboxylic acid and 0.90 g of methyl glycinate hydrochloride in 50 ml of methylene chloride, followed by further adding 10 minutes later 1.64 g of water-soluble carbodiimide hydrochloride. The resultant mixture was stirred at 0° C. for 0.5 hour and, then at room temperature for 20 hours. The reaction mixture was washed with 5% hydrochloric acid, saturated sodium bicarbonate, and saturated saline, dried over anhydrous magnesium sulfate, and concentrated. The residue was purified by a silica gel column chromatography (eluting solution: chloroform-methanol) to give 1.87 g of methyl N-(9-fluorenylcarbonyl)glycinate.

b) Preparation of N-(9-fluorenylcarbonyl)glycine 4.2 ml of 1N sodium hydroxide was added dropwise under ice-cooling to a solution of 900 mg of methyl N-(9-fluorenylcarbonyl)glycinate in 55 ml of ethanol. The resultant mixture was stirred at room temperature for 1.5 hours. The residue obtained by concentrating the reaction mixture was dissolved in 0.5N sodium hydroxide, and washed with an ether. Under ice-cooling, the pH value of the aqueous layer was adjusted to 3 to 4 with 5% hydrochloric acid, and the precipitate formed was separated by filtration. The precipitate thus separated was washed with water and, then, recrystallized from a mixture of ethanol and ether to give 463 mg of N-(9-fluorenylcarbonyl)glycine as white needles.

c) Preparation of 2-[[[N-(9-fluorenylcarbonyl)glycyl]-L-valyl]amino]-6-methylbenzoic acid 84 mg of 2-[[[N-(9-fluorenylcarbonyl)glycyl]-L-valyl]amino]-6-methylbenzoic acid was prepared exactly as in step c) of Example 3, except that 126 mg of 6-methyl-2-(L-valylamino)benzoic acid was subjected to a condensation reaction with 188 mg of N-(9-fluorenylcarbonyl)glycine in place of 9-fluorenyloxyacetic acid used in Example 3.

d) Preparation of 2-[1(S)-[[N-(9-fluorenylcarbonyl)glycyl]amino]-2-methylpropyl]-5-methyl-4H-3,1-benzoxazin-4-one 33 mg of water-soluble carbodiimide hydrochloride was added under ice-cooling to a solution of 72 mg of 2-[[[N-(9-fluorenylcarbonyl)glycyl]-L-valyl]amino]-6-methylbenzoic acid in 3 ml of N,N-dimethylformamide. The mixture was stirred at 0° C. for 0.5 hour and, then, at room temperature for 18 hours. The mixture was concentrated to give a residue which was purified by a silica gel column chromatography (eluting solution: methylene chlorideether) to afford 60 mg of 2-[1(S)-[[N-(9-fluorenylcarbonyl)glycyl]amino]-2-methylpropyl]-5-methyl-4H-3,1-benzoxazin-4-one as a white powder (see Table 1).

EXAMPLE 5

Synthesis of 2-[1(S)-[[N-acetyl-N-(9-fluorenyl)-β-alanyl]amino]-2-methylpropyl]-5-methyl-4H-3,1-benzoxazin-4-one (compound 5)

a) Preparation of N-(9-fluorenyl)-β-alanine ethyl ester 1.0 ml of ethyl acrylate was added to a solution of 9-aminofluorene (1.24 g) in ethanol (20 ml). The resultant mixture was stirred at 80° C. for 5 hours and, then, at room temperature for 36 hours. The residue obtained by condensing the reaction mixture was dissolved in methylene chloride and, then, washed with saturated saline, dried over anhydrous magnesium sulfate, and concentrated. The residue was purified by a silica gel column chromatography (eluting solution: methylene chloride-ether) to give 1.25 g of N-(9-fluorenyl)-β-alanine ethyl ester.

b) Preparation of N-acetyl-N-(9-fluorenyl)-β-alanine ethyl ester 0.51 mg of triethylamine and 0.28 ml of acetyl chloride were added under ice-cooling to a solution of 0.77 g of N-(9-fluorenyl)-β-alanine ethyl ester in 25 ml of methylene chloride. The resultant mixture was stirred at 0° C. for 0.5 hour and, then, at room temperature for 3 hours. The reaction solution was poured into ice-cold 1N hydrochloric acid and extracted with methylene chloride. The organic layer was washed with saturated sodium bicarbonate and saturated saline, dried over anhydrous magnesium sulfate, and concentrated. The residue was purified by a silica gel column chromatography (eluting solution: chloroform-methanol) to give 0.85 g of N-acetyl-N-(9-fluorenyl)-β-alanin ethyl ester.

c) Preparation of N-acetyl-N-(9-fluorenyl)-β-alanine 1.6 ml of 1N sodium hydroxide was added dropwise to a solution of 435 mg of N-acetyl-N-(9-fluorenyl)-β-alanine ethyl ester in 25 ml of ethanol under ice-cooling. After stirring for 4.5 hours, the reaction solution was condensed. The residue was dissolved in water and, then, washed with ether. The pH value of the water layer was adjusted to 3 to 4 with 5% hydrochloric acid. The precipitate formed was separated by filtration, washed with ice-cold water, and recrystallized from a mixture of ethyl acetate and methanol to give 168 mg of N-acetyl-N-(9-fluorenyl)-β-alanine.

d) Preparation of 2-[[[N-acetyl-N-(9-fluorenyl)-β-alanyl]-L-valyl]amino]-6-methylbenzoic acid 192 mg of 2-[[[N-acetyl-N-(9-fluorenyl)-β-alanyl]-L-valyl]amino]-6-methylbenzoic acid was obtained exactly as in step (c) of Example 3, except that 149 mg of N-acetyl-N-(9-fluorenyl)-β-alanine, which was used in place of 9-fluorenyloxyacetic acid used in Example 3, was subjected to a condensation reaction with 91 mg of 6-methyl-2-(L-valylamino)benzoic acid.

e) Preparation of 2-[1(S)-[[N-acetyl-N-(9-fluorenyl)-β-alanyl]amino]-2-methylpropyl]-5-methyl-4H-3,1-benzoxazin-4-one 66 mg of 2-[1(S)-[[N-acetyl-N-(9-fluorenyl)-β-alanyl]amino]-2-methylpropyl]-5-methyl-4H-3,1-benzoxazin-4-one, which was a white foamed solid as indicated in Table 1, was obtained exactly as in step (d) of Example 4 by subjecting 91 mg of 2-[[[N-acetyl-N-(9-fluorenyl)-β-alanyl]-L-valyl]amino]-6-methylbenzoic acid to a dehydration cyclization by using water-soluble carbodiimide hydrochloride.

EXAMPLE 6

Synthesis of 2-{1(S)-[(fluorene-Δ$^9$, $^\alpha$-acetyl) amino]-2-methylpropyl}-5-methyl-4H-3,1-benzoxazin-4-one (compound 6)

a) Preparation of methyl fluorene-Δ$^9$, $^\alpha$-acetate

A suspension of 20 g of 9-fluorenone and 63.1 g of methyl (triphenylphosphoranylidene)acetate in 400 ml of toluene was subjected to reflux under heating for 139 hours. The residue obtained by concentrating the reaction mixture was purified by a silica gel column chromatography (eluting solution: methylene chloride-hexane) to give 23.63 g of methyl fluorene-Δ$^9$, $^\alpha$-acetate as a yellow crystal.

b) Preparation of fluorene-Δ$^9$, $^\alpha$-acetic acid 130 ml of 1N sodium hydroxide was added dropwise under ice-cooling to a suspension of 11.8 g of methyl fluorene-Δ$^9$, $^\alpha$acetate in 600 ml of mechanol. After stirring at room temperature for 3 days, the reaction mixture was concentrated, followed by water addition and, then, washing with ether. The pH value of the aqueous layer was adjusted to 1 under ice-cooling with concentrated hydrochloric acid (about 35%). The precipitate was separated by filtration, washed with water until the filtrate became neutral in pH value, and recrystallized from ethyl acetate to give 10.18 g of fluorene-$\Delta^9$, $\alpha$-acetic acid.

c) Preparation of 2-{1(S)-[(tert-butoxycarbonyl)amino]-2-methylpropyl}-5-methyl-4H-3,1-benzoxazin-4-one 23.7 ml of N-methylmorpholine and 26.3 ml of isobutyl chloroformate were successively added to a solution of 46.8 g of N-(tert-butoxycarbonyl)-L-valine in 250 ml of tetrahydrofuran at −15° C. under a nitrogen atmosphere. After stirring for 1.5 hours, a solution of 23.27 g of 2-amino-6-methylbenzoic acid and 20.3 ml of N-methylmorpholine in 350 ml of N,N-dimethylformamide was added. The resultant mixture was stirred for 1 hour at −15° C., followed by further stirring at room temperature for 18 hours. The reaction mixture was poured into 500 ml of 10% citric acid and extracted with ethyl acetate. The organic layer was washed with saturated saline and dried over anhydrous magnesium sulfate, followed by concentration to give a residue.

60 g of water-soluble carbodiimide hydrochloride was added to a solution of the residue in 500 ml of N,N-dimethylformamide under ice-cooling, followed by stirring the resultant mixture at 0° C. for 2 hours and, then, at room temperature for 18 hours. The residue obtained by concentrating the reaction mixture was purified by a silica gel column chromatography (eluting solution: methylene chloride-ether) to give 20.55 g of 2-{1(S)[(tert-butoxycarbonyl)amino]-2-methylpropyl}-5-methyl-4H-3,1-benzoxazin-4-one as a white powder.

d) Preparation of 2-{1(S)-[(fluorene-$\Delta^9$, $\alpha$-acetyl) amino]-2-methylpropyl}-5-methyl-4H-3,1-benzoxazin-4-one 66.7 ml of 4N hydrochloric acid-1,4-dioxane solution was added dropwise to a solution of 9.31 g of 2-{1(S)-[(tert-butoxycarbonyl)amino]-2-methylpropyl}-5-methyl-4H-3,1-benzoxazin-4-one in 50 ml of 1,4-dioxene with stirring at 0° C. After stirring at 0° C. for 0.75 hour, the reaction mixture was concentrated. 6.25 g of fluorene-$\Delta^9$, $\alpha$-acetic acid was added to the residue and dissolved in 150 ml of N,N-dimethylformamide. Then, 3.3 ml of N-methylmorpholine, 4.72 g of 1-hydroxybenzotriazole, and 5.91 g of water-soluble carbodiimide hydrochloride were successively added to the resultant solution under ice-cooling. After stirring at room temperature for 18 hours, the reaction solution was condensed, and the residue was purified by a silica gel column chromatography (eluting solution: methylene chloride-ether), followed by recrystallization from chloroform-hexane to give 5.76 g of 2-{1(S)-[(fluorene-$\Delta^9$, $\alpha$-acetyl) amino]-2-methylpropyl}-5-methyl-4H-3,1-benzoxazin-4-one: mp 223.5°–224.3° C., (see Table 1).

EXAMPLE 7

Synthesis of 2-[(9-fluorenyloxyacetyl)aminomethyl]-5-methyl-4H-3,1-benzoxazin-4-one (Compound 7)

a) Preparation of 2-[(tert-butoxycarbonyl) aminomethyl]-5-methyl-4H-3,1-benzoxazin-4-one 2.03 ml of N-methylmorpholine and 2.25 ml of isobutyl chloroformate were successively added to 25 ml of a tetrahydrofuran solution containing 3.26 g of N-(tert-butoxycarbonyl)glycine at −15° C. under a nitrogen atmosphere. The resultant mixture was stirred for 0.5 hour, followed by adding dropwise into the mixture 35 ml of N,N-dimethylformamide solution containing 2.0 g of 2-amino-6-methylbenzoic acid and 1.74 ml of N-methylmorpholine. The resultant mixture was stirred for 0.5 hour. After additional stirring at room temperature for 3 hours, the reaction mixture was poured into 10% citric acid and extracted with ethyl acetate. The organic layer was washed with saturated saline, dried over anhydrous magnesium sulfate, and concentrated to give a residue.

4.18 g of water-soluble carbodiimide hydrochloride was added under ice-cooling to 60 ml of N,N-dimethylformamide solution containing 6.73 g of the residue. The resultant mixture was stirred at 0° C. for 2 hours. The residue obtained by concentrating the reaction mixture was purified by a silica gel column chromatography (eluting solution: hexane-ethyl acetate) to give 2.93 g of 2-[(tert-butoxycarbonyl) aminomethyl]-5-methyl-4H-3,1-benzoxazin-4-one as a white powder.

b) Preparation of 2-[(9-fluorenyloxyacetyl)aminomethyl]-5-methyl-4H-3,1-benzoxazin-4-one 3.0 ml of a 50% trifluoroacetic acid-methylene chloride solution was added dropwise under ice-cooling to 106.7 mg of 2-[(tert-butoxycarbonyl)aminomethyl]-5-methyl-4H-3,1-benzoxazin-4-one with stirring. After stirring at 0° C. for 0.67 hour, the mixture was concentrated to give 119 mg of trifluoroacetic acid salt of 2-(aminomethyl)-5-methyl-4H-3,1-benzoxazin-4-one. To the salt was added 78 mg of 9-fluorenyloxyacetic acid and dissolved in 3.0 ml of N,N-dimethylformamide. 35.8 $\mu$l of N-methylmorpholine, 48.5 mg of 1-hydroxybenzotriazole and 68.7 mg of water-soluble carbodiimide hydrochloride were successively added to the solution under ice-cooling. The resultant mixture was stirred at room temperature for 18 hours. The reaction mixture was concentrated to give a residue which was purified by a silica gel column chromatography (eluting solution: hexane-ethyl acetate) to afford 15.4 mg of 2-[(9-fluorenyloxyacetyl)aminomethyl]-5-methyl-4H-3,1-benzoxazin-4-one (see Table 1).

EXAMPLE 8

Synthesis of 2-{1-[(9-fluorenyloxyacetyl)amino]-1-methylethyl}-5-methyl-4H-3,1-benzoxazin-4-one (Compound 8)

a) Preparation of N-(tert-butoxycarbonyl)-2-aminoisobutyric acid 20.6 g of 2-aminoisobutyric acid was dissolved in 600 ml of a mixture of 1,4-dioxane and water (5:1). To the solution were added 250 ml of 1N sodium hydroxide and 54.61 g of di-tert-butyl dicarbonate with stirring under ice-cooling. After stirring at room temperature for 48 hours, concentration of the mixture gave a residue. 500 ml of 5% potassium bisulfate was added under ice-cooling to the residue so as to adjust the pH value to 3 to 4, followed by extraction with ethyl acetate. The organic layer was dried over anhydrous magnesium sulfate and concentrated to give a residue which was recrystallized from 400 ml of hexane to afford 25.99 g of N-(tert-butoxycarbonyl)-2-aminoisobutyric acid.

b) Preparation of
2-{1-[(tert-butoxycarbonyl)amino]-1-methylethyl}-5-methyl-4H-3,1-benzoxazin-4-one 8.3 ml of N-methylmorpholine and 9.6 ml of isobutyl chloroformate were successively added to a solution of 15 g of N-(tertbutoxycarbonyl)-2-aminoisobutyric acid in 80 ml of tetrahydrofuran.

After stirring for 0.83 hour, a solution of 7.97 g of 2-amino-6-methylbenzoic acid and 7.7 ml of N-methylmorpholine in 80 ml of N,N-dimethylformamide was added and the resultant mixture was stirred for 18 hours.

After the reaction solution was concentrated, 250 ml of 5% potassium bisulfate was added to the residue, followed by extraction with ethyl acetate. The organic layer was washed with saturated saline, dried over anhydrous magnesium sulfate, and concentrated to give 26.13 g of a residue. To a solution of the residue in 150 ml of methylene chloride was added 20.0 g of water-soluble carbodiimide hydrochloride and the mixture was stirred for 18 hours at room temperature. The residue obtained by concentrating the reaction mixture was purified by a silica gel column chromatography (eluting solution: methylene chloride-ether) to afford 5.65 g of 2-{1-[(tert-butoxycarbonyl)amino]-1-methylethyl}-5-methyl-4H-3,1-benzoxazin-4-one c) Preparation of
2-{1-[(9-fluorenyloxyacetyl)amino]-1-methylethyl}-5-methyl-4H-3,1-benzoxazin-4-one 250 ml of a 50% trifluoroacetic acid-methylene chloride solution was added dropwise under ice-cooling to 5.63 g of 2-{1-[(tert-butoxycarbonyl)amino]-1-methylethyl}-5-methyl-4H-3,1-benzoxazin-4-one with stirring. The mixture was stirred at 0° C. for 0.58 hour, and concentration of the mixture gave a residue which was dissolved in 80 ml of a 4N hydrochloric acid-1,4-dioxane solution at 0° C. After stirring for 0.58 hour, the reaction mixture was subjected to azeotropic distilation with toluen so as to give the hydrochloride salt of 2-(1-amino-1-methylethyl)-5-methyl-4H-3,1-benzoxazin-4-one. To the salt was added 4.47 g of 9-fluorenyloxyacetic acid, and dissolved in 180 ml of N,N-dimethylformamide. To the mixture were added successively at room temperature 2.2 ml of N-methylmorpholine, 2.98 g of 1-hydroxybenzotriazole and 5.09 g of a water-soluble carbodiimide hydrochloride. After stirring for 18 hours, the reaction mixture was concentrated to give a residue which was purified by a silica gel column chromatography (eluting solution: methylene chloride-ether), followed by recrystallization from methylene chloride-ether to give 6.34 g of 2-{1-[(9-fluorenyloxyacetyl)amino]-1-methylethyl}-5-methyl-4H-3,1-benzoxazin-4-one: mp 162.1°–162.8° C. (see Table 1).

EXAMPLE 9

Synthesis of
2-{1-[(9-fluorenyloxyacetyl)amino]-1-ethylpropyl}-5-methyl-4H-3,1-benzoxazin-4-one (compound 9)

Compound 9 was synthesized as in Example 8, except that 4.59 g of sodium salt of 2-amino-2-ethylbutyric acid was used in place of 2-aminoisobutyric acid used in Example 8 (See Table 1).

EXAMPLE 10

Synthesis of
2-{1-[(9-fluorenyloxyacetyl)amino]cyclohexyl}-5-methyl-4H-3,1-benzoxazin-4-one (compound 10)

Compound 10 was synthesized as in Example 8, except that 4.29 g of 1-amino-1-cyclohexanecarboxylic acid was used in place of 2-aminoisobutyric acid used in Example 8 (See Table 1).

Table 1 shows the chemical structures and physicochemical properties of the compounds manufactured in the Examples described above.

Needless to say, the present invention is not restricted the Examples described above. For example, the compounds shown in Table 2 also fall within the technical scope of the present invention.

TABLE 1

| | Structure | Properties | ¹HNMR(CDCl₃, δ value) | MS (m/z) |
|---|---|---|---|---|
| Compound 1 | 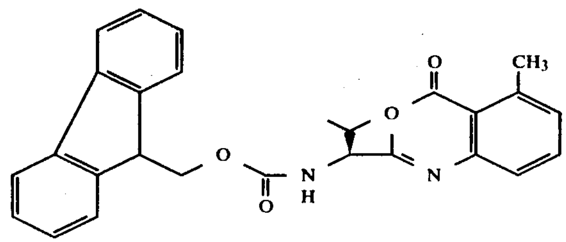 | white foam | 0.97(3H, d, J = 6.8 Hz), 1.05(3H, d, J = 6.7 Hz), 2.37(1H, m), 2.80(3H, s), 4.26(1H, t, J = 7.2 Hz), 4.45(2H, d, J = 7.2 Hz), 4.61(1H, dd, J = 9.2, 5.4 Hz), 5.53(1H, d, J = 9.2 Hz), 7.26–7.45(6H, m), 7.64(2H, m), 7.65(1H, t, J = 7.8 Hz), 7.77(2H, d, J = 7.5 Hz). | EI-MS: 454(M⁺), 178, 160. |
| Compound 2 | 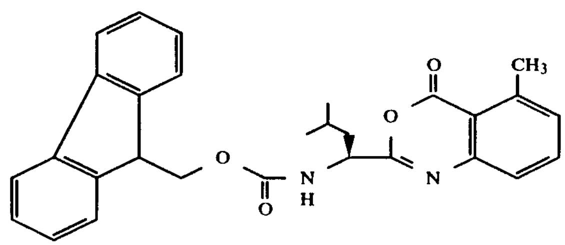 | white foam | 0.99(3H, d, J = 5.5 Hz), 1.01(3H, d, J = 5.5 Hz), 1.6–1.8(3H, m), 2.80(3H, s), 4.25(1H, t, J = 6.4 Hz), 4.44(2H, m), 4.75(1H, m), 5.39(1H, d, J = 9.1 Hz), 7.29–7.43(6H, m), 7.63(2H, m), 7.64(1H, t, J = 7.8 Hz), 7.77(2H, d, J = 7.5 Hz). | EI-MS: 468(M⁺), 178, 160. |
| Compound 3 | 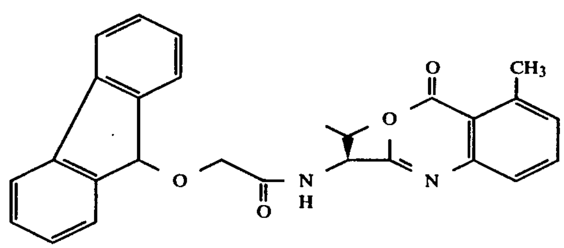 | white powder mp: 146.2–147.6° C. | 1.02(3H, d, J = 6.8 Hz), 1.04(3H, d, J = 6.8 Hz), 2.38(1H, m), 2.82(3H, s), 3.66(1H, d, J = 15.3 Hz), 3.79(1H, d, J = 15.3 Hz), 4.87(1H, dd, J = 9.3, 5.7 Hz), 5.81(1H, s), 7.25–7.71(12H, m). | CI-MS: 455(MH⁺), 291. |
| Compound 4 | 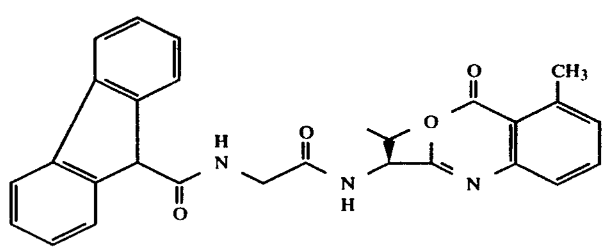 | white powder mp: 170.8–173.6° C. | 0.87(3H, d, J = 6.8 Hz), 0.94(3H, d, J = 6.8 Hz), 2.27(1H, m), 2.78(3H, s), 3.93(2H, d, J = 5.6 Hz), 4.76(1H, dd, J = 8.8, 5.3 Hz), 4.89(1H, s), 6.02(1H, t, J = 5.6 Hz), 6.61(1H, d, J = 8.8 Hz), 7.29–7.81(11H, m). | EI-MS: 481(M⁺), 316, 274, 233, 192, 165, 160, 155. |

TABLE 1-continued

| Structure | Properties | $^1$HNMR(CDCl$_3$, δ value) | MS (m/z) |
|---|---|---|---|
| Compound 5 | white foam | 0.84, 0.89, 0.93 & 0.94 (total 6H, d, each, J = 6.8 Hz), 1.90(1H, m), 2.1–2.3(2H, m), 2.35 & 2.58(total 3H, s each), 2.77 & 2.79(total 3H, s each), 2.9–3.1(total 1H, m), 3.15–3.4(total 1H, m), 4.63(1H, m), 5.50 & 6.79(total 1H, d each, J = 9.0 Hz), 5.85 & 6.98(total 1H, s each), 7.28–7.76(11H, m). 1:1 mixture of cis- and trans-acetoamide | EI-MS: 509(M$^+$), 466, 234, 192, 180, 165, 160. |
| Compound 6 | white powder mp: 223.5–224.3° C. | 1.06(3H, d, J = 6.8 Hz), 1.12(3H, d, J = 6.8 Hz), 2.45(1H, m), 2.80(3H, s), 5.09(1H, dd, J = 8.7, 5.4 Hz), 6.64(1H, d, J = 8.7 Hz), 6.84(1H, s), 7.21–7.43(7H, m), 7.63(2H, d, J = 7.6 Hz), 7.70(1H, d, J = 7.6 Hz), 8.71(1H, d, J = 7.8 Hz). | FAB-MS: 437(MH$^+$) 205. |
| Compound 7 | white powder low melting point | 2.81(3H, s), 3.78(2H, s), 4.43(2H, d, J = 5.2 Hz), 5.78(1H, s), 7.26–7.69(12H, m). | EI-MS: 413 (MH$^+$), 232, 190. |
| Compound 8 | white powder mp: 162.1–162.8° C. | 1.78(6H, s), 2.80(3H, s), 3.75(2H, s), 5.77(1H, s), 7.3–7.45(6H, m), 7.6–7.7(5H, m), 7.90(1H, br.s.). | FAB-MS: 441 (MH$^+$). |

TABLE 1-continued

| | Structure | Properties | ¹HNMR(CDCl₃, δ value) | MS (m/z) |
|---|---|---|---|---|
| Compound 9 | | Colorless Oil | 0.74(6H, t, J = 7.4 Hz), 1.97–2.09(2H, m), 2.57–2.69(2H, m), 2.83(3H, s), 3.71 (2H, s), 5.83(1H, s), 7.27–7.51(7H, m), 7.67–7.73(4H, m), 8.37(1H, s). | FAB-MS: 469(MH⁺). |
| Compound 10 | | white foam | 1.45–1.85(6H, m), 2.0–1.15(2H, m), 1.25–1.35(2H, m), 2.76(3H, s), 3.69(2H, s), 5.77(1H, s), 7.02(1H, s), 7.23(1H, d, J = 7.5 Hz), 7.3–7.45(5H, m), 7.5–7.75(5H, m). | FAB-MS: 481(MH⁺). |

TABLE 2
| | Structure |
|---|---|
| Compound 11 | 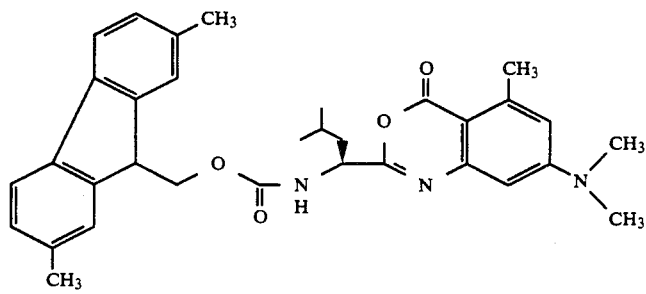 |
| Compound 12 | 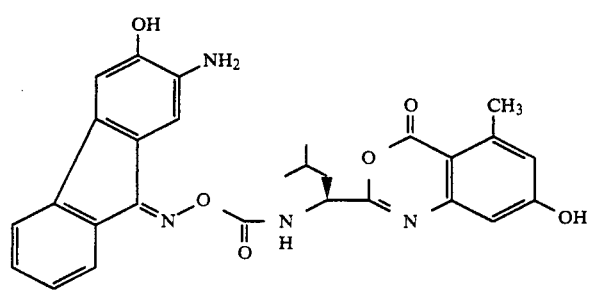 |
| Compound 13 | 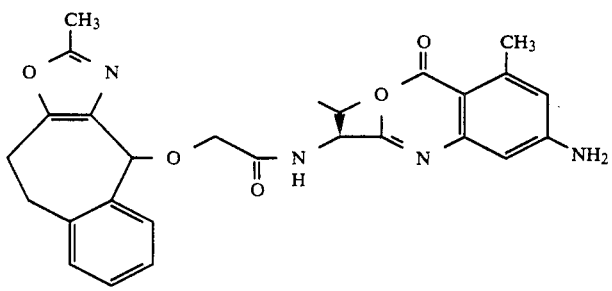 |
| Compound 14 | 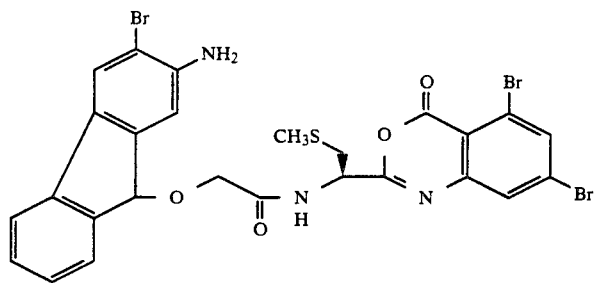 |
| Compound 15 | 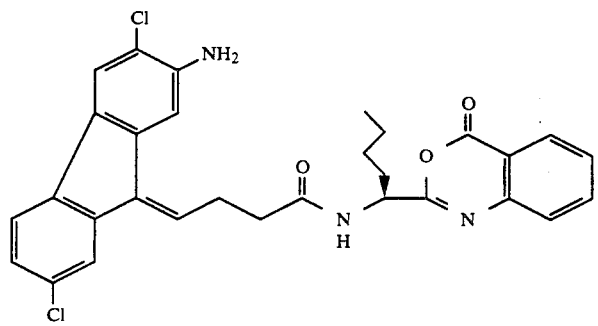 |

TABLE 2-continued

| | Structure |
|---|---|
| Compound 16 | 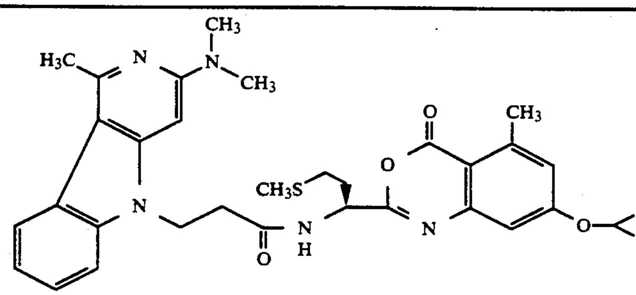 |
| Compound 17 | 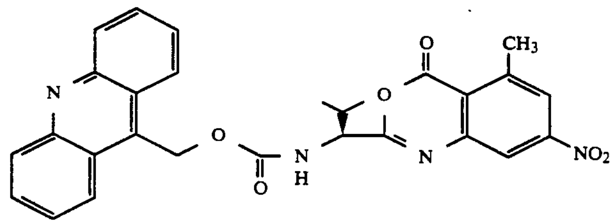 |
| Compound 18 | 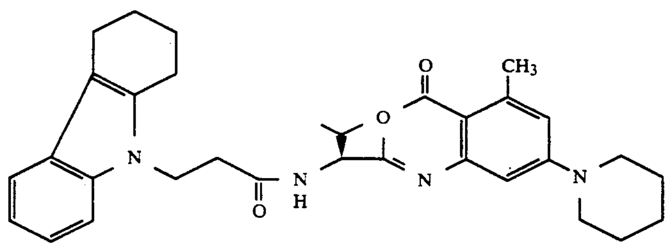 |
| Compound 19 | 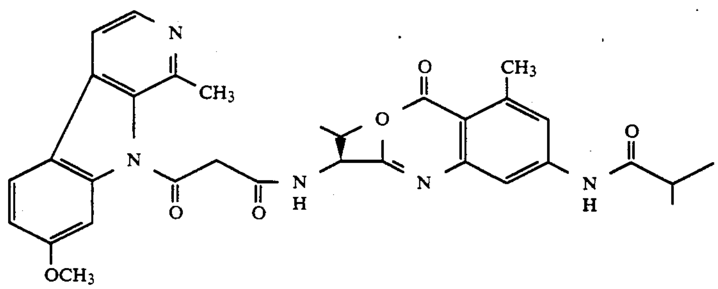 |
| Compound 20 | 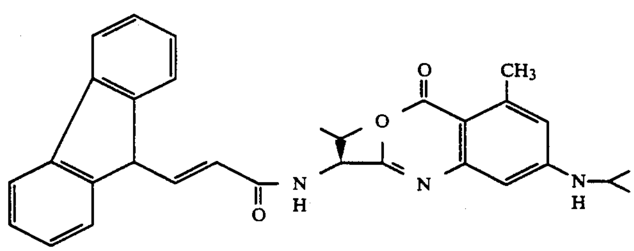 |
| Compound 21 | 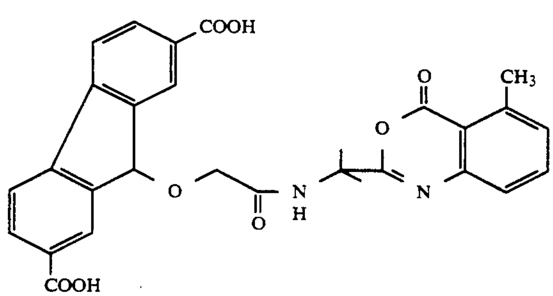 |

TABLE 2-continued
| Structure |
|---|
| Compound 22 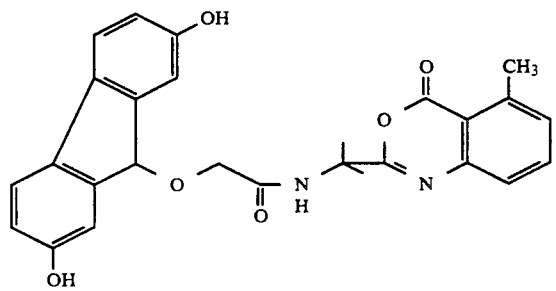 |
| Compound 23 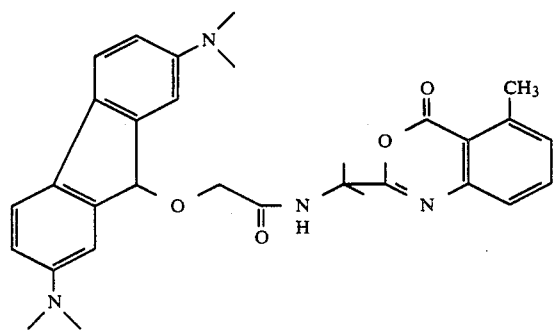 |
| Compound 24 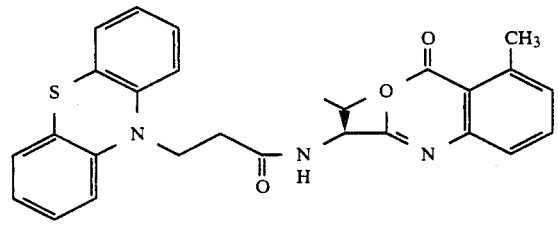 |
| Compound 25 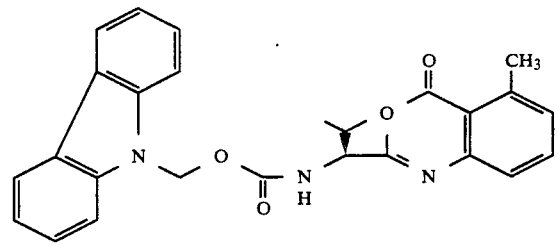 |
| Compound 26 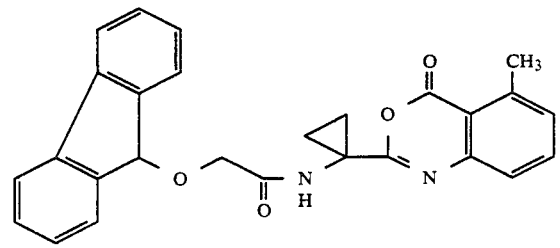 |

TABLE 2-continued

| | Structure |
|---|---|
| Compound 27 | 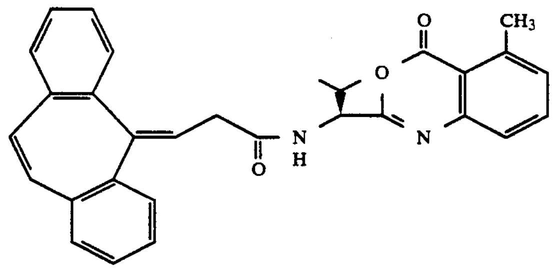 |
| Compound 28 | 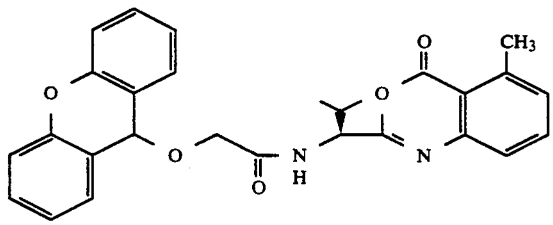 |
| Compound 29 | 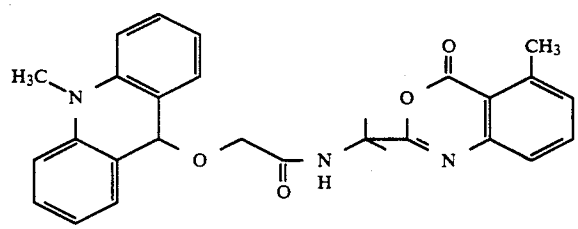 |
| Compound 30 | 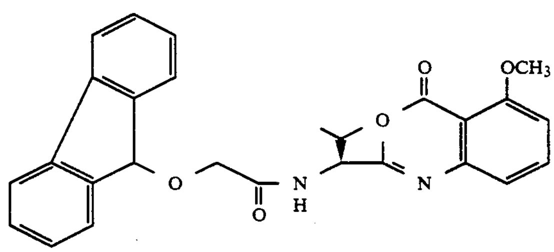 |

The novel oxazinone derivative of the present invention represented by formula (I) was tested for the protease inhibiting activity, the activity for suppressing the neutrophil chemotaxis, and the effect for suppressing the carrageenin-induced air pouch inflammation, as follows.

Test 1: Serine Protease Inhibiting Activity

Inhibotory activities of the oxadinone derivative of the present invention against human leukocyte elastase (HLE), human sputum elastase (HSE), human cathepsin G (HCG), bovine pancreatic α-chymotrypsin (CYT) and bovine pancreatic trypsin (TRY) were measured as follows:

(1) Measurement of HLE Inhibitory Activity a) Enzyme Preparing Method

A buffy coat was obtained by subjecting human vein blood to centrifugal separation, followed by adding distilled water to the buffy coat thus obtained for performing a low tension treatment so as to collapse erythrocytes. A mixture consisting of 10 parts of a 33.4% Conrey 400 solution and 24 parts of 9% of Ficoll solution was added to the residual blood cell component, followed by applying a density gradient centrifugal operation so as to obtain neutrophils. The neutrophil fraction was washed three times with Hanks' buffer so as to recover cells, which were frozen at −80° C. for preservation until the cells were used. The cells preserved under a frozen state were thawed with warm water of 37° C. and suspended in the lysis buffer (0.1M Tris-HCl pH 7.5, 1M MgCl$_2$, 0.1% Brij 35), the amount of the buffer being 9 times as much as that of the cells. Then, the suspended cells were collapsed with polotron while cooling the suspension with ice. Then, the suspension was subjected to a centrifugal separation at 100,000×g for one hour so as to remove the precipitate. Also, a buffer (5 mM Tris-HCl pH 7.5, 1M NaCl, 1.1% Brij 35) was added to the supernatant in an amount twice as much as the supernatant so as to prepare a crude solution of an enzyme extract. The crude solution of an enzyme extract was adsorbed on an aprotinin affinity column. Further, the active fraction eluted with a 50 ml glycine-HCl solution (pH 3.3, 1M NaCl, 0.1% Brij 35) was passed through a MONO S ion-exchange chromatography. The active fraction eluted with a 2M NaCl linear gradient was dialyzed and, then, subjected to a freeze-drying so as to prepare an enzyme sample.

b) Method for Evaluating Enzyme Inhibiting Activity

A test compound to be detected was dissolved in DMSO (for fluorometry) so as to prepare solutions of various concentrations. Then, the solution of 0.2M Tris-HCl (pH 9.6) was added to each of the solutions in an amount twice as much as the solution so as to prepare a test solution. On the other hand, a synthetic substrate (MeOSuc-Ala-Pro-Val-pNA; FUNAKOSHI) was dissolved in DMSO, followed by adding 0.2M tris-HCl solution (pH 8.6) to the solution in an amount twice as much as the solution so as to prepare a substrate solution.

A microplate (NUNK) provided with 96 wells was used for the reaction. The reaction was repeatedly carried out 6 times for each concentration of the test compound. Each of 140 μl of the enzyme solution (0.2M Tris-HCl, pH 8.6), 30 μl of the test material solution and 30 μl of the substrate solution was pre-incubated for 10 minutes at 37° C. for each well of the microplate. After incubation of a mixture of the enzyme solution and the test material solution for 10 minutes, the substrate solution was added so as to carry out the enzyme reaction. For determining the substrate decomposition, the absorbance (405 run) of the released pNA was measured by a microplate reader (MTP-100; CORONA), and the substrate decomposition was calculated on the basis of the average value of the absorbances repeatedly measured 6 times. The inhibitory concentration of the test compound relative to the decomposition amount of the substrate in the case where the test compound was not added was obtained as $IC_{50}$ value. The final concentrations of HLE and the synthetic substrate in the reacting solution were found to be 5.63 nM and 0.2625 mM, respectively.

(2) Measurement of HSE Inhibiting Activity a) Enzyme Preparing Method Bought from Sigma Inc.

b) Method for Evaluating Enzyme Inhibiting Activity

Employed was a measuring method similar to that described previously in conjunction with the measurement of the HLE inhibitory activity, except that used was a buffer solution of pH 7.0. The final concentrations of HSE and the synthetic substrate (MeOSuc-Ala-Ala-Pro-Phe-pNA; FUNAKOSHI) in the solution of the enzyme reaction were 10 nM and 0.25 mM, respectively.

(3) Measurement of HCG Inhibitory Activity a) Enzyme Preparing Method Bought from Cosmo Bio Inc.

b) Method for Evaluating Enzyme Inhibiting Activity

Employed was a measuring method similar to that described previously in conjunction with the measurement of the HLE inhibitory activity, except that used was a buffer solution of pH 7.5. The final concentrations of HCG and the synthetic substrate (Ac-Ala-Ala-Pro-Phe-pNA; FUNAKOSHI) in the solution of the enzyme reaction were 50 nM and 0.5 mM, respectively.

(4) Measurement of CYT Inhibitory Activity a) Enzyme Preparing Method Bought from Sigma Inc.

b) Method for Evaluating Enzyme Inhibitory Activity

Employed was a measuring method similar to that described previously in conjunction with the measurement of the HLE inhibiting activity, except that used was a buffer solution of pH 8.0. The final concentrations of CYT and the synthetic substrate (Ac-Ala-Ala-Pro-Phe-pNA; FUNAKOSHI) in the solution of the enzyme reaction were 3.4 nM and 0.273 mM, respectively.

(5) Measurement of TRY Inhibitory Activity a) Enzyme Preparing Method Bought from Sigma Inc.

b) Method for Evaluating Enzyme Inhibiting Activity

Employed was a measuring method similar to that described previously in conjunction with the measurement of the HLE inhibiting activity, except that used was a buffer solution of pH 7.5. The final concentrations of TRY and the synthetic substrate (Z-Arg-pNA; FUNAKOSHI) in the solution of the enzyme reaction were 25 nM and 1.0 mM, respectively.

Results

Table 3 shows the results of 1) to 5) described above

TABLE 3

Inhibitory Activity of compounds on several kinds of protease

| Compound | $IC_{50}$ value (μM) | | | | |
|---|---|---|---|---|---|
| | HLE | HSE | HCG | CYT | TRY |
| 1 | 0.24 | 0.31 | >5.5 | 4.75 | >6.89 |
| 2 | 0.73 | 0.30 | >5.34 | 4.46 | >6.68 |
| 3 | 0.51 | — | >27.5 | 3.43 | — |
| 4 | 0.75 | — | 11.3 | 6.58 | — |
| 5 | 0.24 | — | >12.3 | 1.96 | — |
| 6 | 0.64 | — | — | — | — |
| 7 | 1.28 | — | >7.59 | >7.59 | — |
| 8 | 1.00 | — | — | — | — |

As apparent from Table 3, the compound of the present invention represented by formula (I) exhibits a strong selective inhibiting activity with respect to serine protease, particularly, human neutrophil elastase.

Test 2: Activity of the Invented Compound for Suppressing Chemotaxis of Human Neutrophils A neutrophil fraction (60% percoal fraction having neutrophil purity of at least 90%) was obtained from a human peripheral blood by a percoal density gradient centrifugal separation (2300 rpm, 20 minutes).

1300 μl of a culture medium containing $10^{-7}$M of fMLP (formylmethionyloycyl-phenylalanine), which is a neutrophil chemotaxis factor, was added in advance to each well of a chemotaxis chamber (KURABO). An inter cell having pores 5 μm in diameter and containing $8 \times 10^5$ neutrophils and the compound of the present invention adjusted at a desired concentration was disposed in the chemotaxis chamber. After culturing for one hour at 37° C. within a culturing device containing 5% of carbon dioxide gas, the number of cells migrated from the upper side of inter cell membrane into the lower side of the membrane in the chamber was counted by the method described in the following. Specifically, the lower side surface of the inter cell membrane was washed 4 times with PBS. After fixing the washed surface with methanol, the cells were dyed with hematoxylin-eosine solution. Then, the membrane was removed from the inter cell and put on a sliding glass for air-drying, followed by sealing with Canada balsam. Under this condition, five areas selected at random of the membrane were microscopically observed so as to count the number of cells. An average of the number of cells within the five areas was calculated so as to determine the number of migrated cells.

The function of the invented compound for suppressing chemotaxis was determined by the formula given below, in which the value obtained by subtracting the number of migrating cells in the reference experiment in which fMLP was not added from the number of migrating cells in the experiment in which the compound of the present invention was not added was set at 100:

Activity for suppressing chemotaxis (%)
= 100 − A/B × 100
= 100 − (C − D)/(E − D) × 100 where:
A: Chemotaxis in the case of containing the compound of the present invention;
B: Chemotaxis in the case of not containing the compound of the present invention;
C: The number of migrating cells in the case of adding the compound of the present invention, fMLP;
D: The number of migrating cells in the case of not adding fMLP; and
E: The number of migrating cells in the case of adding only fMLP.

TABLE 4

(Suppressive activity of a compound on the Neutrophil Chemotaxis)

| Compound | Concentration (μm) | Chemotaxis | Activity for Suppressing Chemotaxis (%) |
|---|---|---|---|
| 1 | 0 | 100 | — |
|  | 50 | 11 | 89 |
|  | 100 | 1 | 99 |

As apparent from Table 4, the compound of the present invention represented by formula (I) produces a prominent function of suppressing the chemotaxis of the human nuetrophils.

Test: 3 Effect of the Invented Compound for Suppressing Neutrophil Infiltration into carrageenin-induced Air Pouch Inflammation Groups of SD series male rats (5 five weeks old and each weighing 110 to 130 g) were used in this experiment, each group consisting of five rats. In the first step, an air bladder was formed on the back of the rat by hypodermic injection of 8 ml of air while anesthetizing the rat with either. Twenty-four hours later, 5 ml of a physiological saline containing 1% of carrageenin manufactured by Wako K.K. was injected into the air pouch. Promptly after the carrageenin injection, a solution prepared by dissolving the test material (compound of the present invention) in 200 μl of DMSO (dimethylsulfoxide) was administered to the air pouch on the back of the rat.

Five hours later, the rat was killed and the blood was released therefrom. Then, 5 ml of PBS containing 10 mM of EDTA (ethylenediamine tetraacetate) was injected into the air pouch. The exudate within the air bladder was washed and, then, recovered. A predetermined amount of the recovered exudate was measured by a colter counter so as to count the number of infiltrated cells.

The effect of the test material for suppressing the cell infiltration into the carrageenin induced inflammation was determined by the formula given below, in which the value obtained by subtracting the number of infiltrated cells in the experiment in which carrageenin was not administered from the number of infiltrated cells in the reference group in which a medicine was not administered was set at 100:

Rate of Suppressing Cell Infiltration (%):
= 100 − S/T × 100
= 100 − (U − V)/(W − V) × 100 where:
S: Cell infiltration capability in the case of containing the compound of the present invention;
T: Cell infiltration capability in the case of not containing the compound of the present invention;
U: The number of infiltrated cells in the case of administering the compound of the present invention and carrageenin;
V: The number of infiltrated cells in the case of not adding carrageenin; and
W: The number of infiltrated cells in the case of administering carrageenin only.

Table 5 shows the results.

TABLE 5

(The suppressive effect of compounds on the neutrophile infiltration into carrageenin-induced air pouch inflammation.)

| Compound | Amount of Administration (μmol) | Cell Infiltration Capability | Rate (%) of Suppressing Cell Infiltration |
|---|---|---|---|
| Control | 0 | 100 | — |
| 1 | 17 | 62 | 38 |
| 2 | 17 | 76 | 24 |

As apparent from Table 5, the compound of the present invention represented by formula (I) permits suppressing the neutrophil infiltration into the carrageenin-induced air pouch inflammation.

As described above in detail, the oxazinone derivatives of the present invention are novel compounds effectively acting on various stages of inflammatory symptoms so as to suppress the cell infiltration. Particularly, the compounds of the present invention exhibit excellent inhibiting action on elastase. Also, the compounds permit suppressing the chemotaxis of human peripheral blood neutrophils toward chemically attracting substance derived from bacteria. Further, the compounds of the present invention permits suppressing the neutrophil infiltration in an animal inflammatory model.

Under the circumstances, the compounds of the present invention are useful as an anti-inflammatory agent, an agent for suppressing neutrophil infiltration, or as a serine protease inhibitor, making it possible to use the compounds of the present invention as a medicine.

We claim:

1. An oxazinone derivative represented by formula (I) or a pharmaceutically acceptable acid-addition salt thereof:

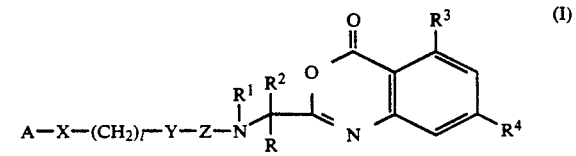

wherein,
$R^1$ is a hydrogen atom, lower alkyl group or lower acyl group;

R and $R^2$, which are the same or different, are a hydrogen atom, lower alkyl group or lower alkylthio lower alkyl group, and optionally together they may form an alicyclic ring;

$R^3$ is a hydrogen atom, lower alkyl group which may be optionally substituted with fluorine, lower alkoxy group or halogen atom;

$R^4$ is a hydrogen atom, lower alkyl group, hydroxyl group, halogen atom, lower alkoxy group, lower alkoxy-carbonyl group, carboxyl group, lower alkylthio group, nitro group, lower acyloxy group or $-NR^5R^6$ ($R^5$ and $R^6$, which are the same or different, being hydrogen atom, lower alkyl group or lower acyl group, or $R^5$ and $R^6$ optionally forming a hetero ring together with the adjacent nitrogen atom, said hetero ring optionally having a substituent);

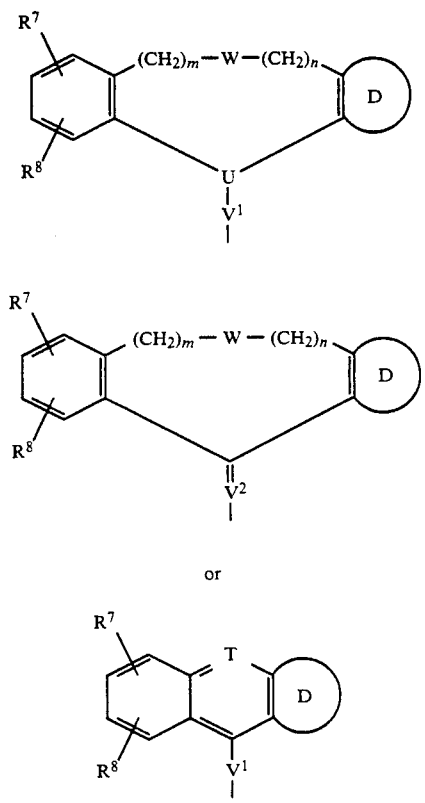

wherein

W is $-O-$, $-S-$, $-CH=CH-$, or $NR^9-$ ($R^9$ being hydrogen atom, lower alkyl group or lower acyl group) or W means that $(CH_2)_m$ is directly bonded to $(CH_2)_n$;

U is

or nitrogen atom;

$V^1$ is $-O-$, $-S-$, $-CO-$, $-CHR^{10}-$ ($R^{10}$ being hydrogen atom, lower alkyl group, lower acyl group), or $-NR^{11}-$ ($R^{11}$ being hydrogen atom, lower alkyl group or lower acyl group), with the proviso that when U is nitrogen atom, $V^1$ is $-CO-$, or $-CHR^{10}-$ ($R^{10}$ being as defined above) or $-NR^{11}-$ ($R^{11}$ being as defined above);

$V^2$ is $=CR^{12}-$ ($R^{12}$ being hydrogen atom, lower alkyl group or lower acyl group) or $=N-$;

T is $=CH-$ or $=N-$;

$R^7$ and $R^8$, which are the same or different, are hydrogen atom, lower alkyl group that may be optionally substituted with fluorine, lower acyl group, halogen atom, hydroxyl group, lower alkoxy group, lower acyloxy group, carboxyl group or $-NR^{13}R^{14}$ ($R^{13}$ and $R^{14}$, which are the same or different, being hydrogen atom, lower alkyl group or lower acyl group);

m and n are independently integers of 0 to 2, with the proviso that $m+n \leq 2$; and D is selected from the group consisting of

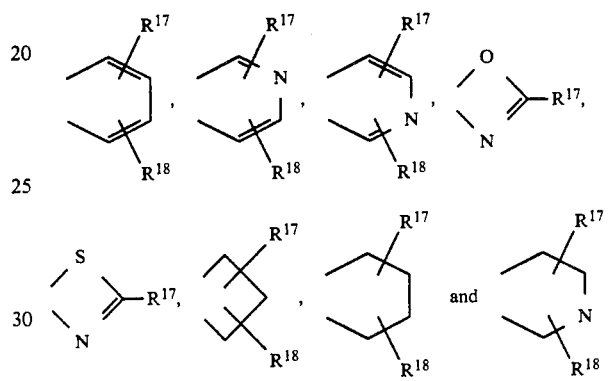

wherein $R^{17}$ and $R^{18}$, which are the same or different, are hydrogen atom, lower alkyl group that may be optionally substituted with flourine, lower acyl group, halogen atom, hydroxyl group, lower alkoxy group, lower acyloxy group, carboxyl group or $-NR^{19}R^{20}$ ($R^{19}$ and $R^{20}$, which are the same or different, being hydrogen atom, lower alkyl group or lower acyl group);

X is $-O-$, $-S-$, $-CO-$ or $-NR^{15}-$ ($R^{15}$ being hydrogen atom, lower alkyl group or lower acyl group) or X means that A is directly bonded to $(CH_2)_l$;

Y is $-O-$, $-CH=CH-$ or $-NR^{16}-$ ($R^{16}$ being hydrogen atom, lower alkyl group or lower acyl group) or Y means that $(CH_2)_l$ is directly bonded to Z;

Z is $-CH_2$ or $-CO-$, with the proviso that when Z is $-CH_2-$, $(CH_2)_l$ is directly bonded to Z; and l is an integer of 0 to 4.

2. A serine protease inhibiting agent, comprising a pharmaceutically acceptable carrier and an amount of the compound defined in claim 1 effective for producing a serine protease inhibiting action.

3. An anti-inflammatory agent, comprising a pharmaceutically acceptable carrier and an amount of the compound defined in claim 1 effective for producing an anti-inflammatory action.

4. An agent for suppressing neutrophil infiltration, comprising a pharmaceutically acceptable carrier and an amount of the compound defined in claim 1 effective for producing the action of suppressing neutrophil infiltration.

* * * * *